United States Patent

Kanesaka et al.

[11] Patent Number: 5,593,394
[45] Date of Patent: Jan. 14, 1997

[54] SHAFT FOR A CATHETER SYSTEM

[76] Inventors: Nozomu Kanesaka, 36 Cathy Rd.;
George A. Tashji, 24 Cathy Rd., both of Hillsdale, N.J. 07642

[21] Appl. No.: 378,247

[22] Filed: Jan. 24, 1995

[51] Int. Cl.$^6$ .................................................. A61M 25/14
[52] U.S. Cl. ............................................................ 604/282
[58] Field of Search ..................................... 604/280, 281, 604/282

[56] References Cited

U.S. PATENT DOCUMENTS

| | | | |
|---|---|---|---|
| 3,957,054 | 5/1976 | McFarlane | 604/282 |
| 4,406,656 | 9/1983 | Hattler et al. | 604/282 |
| 4,713,049 | 12/1987 | Carter | 604/282 |
| 4,717,379 | 1/1988 | Ekholmer | 604/280 |
| 4,834,709 | 5/1989 | Banning et al. | 604/282 |
| 4,841,976 | 6/1989 | Packard et al. | 604/280 |
| 4,955,862 | 9/1990 | Sepetka | 604/282 |
| 4,986,814 | 1/1991 | Burney et al. | 604/281 |
| 5,125,909 | 6/1992 | Heimberger | 604/282 |
| 5,337,733 | 8/1994 | Bauerfeind et al. | 604/282 |

*Primary Examiner*—Paul J. Hirsch
*Attorney, Agent, or Firm*—Kanesaka & Takeuchi

[57] ABSTRACT

A shaft of a catheter system of the invention is used for PTCA, angiography, perfusion, drug delivery or the like in a body of a patient. The shaft is formed of a tube and a plurality of ribs projecting from an inner wall of the tube towards a center thereof. The respective ribs have a certain thickness, so that resisting force against a direction in which the shaft is bent or kinked is provided, and at the same time force or torque for manipulating the catheter system is transmitted from the proximal end to the distal end of the shaft.

4 Claims, 2 Drawing Sheets

SHAFT FOR A CATHETER SYSTEM

BACKGROUND OF THE INVENTION AND RELATED ART STATEMENT

The present invention relates to a shaft of a catheter system for performing intravascular procedures, more particularly to a shaft having excellent flexibility and ability for transmission of torque or force to manipulate the catheter system.

A catheter system or catheter for percutaneous transluminal coronary angioplasty (PTCA), angiography, perfusion, drug delivery or the like is introduced into a body of a patient. The catheter system includes a head portion, a shaft and a handle. When the catheter system is used, the shaft is pushed into a vessel, such as a blood vessel, from the head portion, so that the head portion is located in a desired position away from an entrance thereof by manipulating the handle.

A conventional shaft of the catheter system is formed of a single lumen in a form of a tube or wire. Often, the shaft is required to be stiff to transmit large force or torque for passing through a constricted portion of a blood vessel. Therefore, the lumen or shaft is made stiff. However, the stiff shaft tends to kink when it is manipulated since the single lumen is not enough to hold or support the force required for passing through the constricted portion. The term "kink" used herein means "crash and bend".

In order to solve the above problem, there has been proposed a shaft for a multi-lumen catheter system comprising at least two coaxial lumens, or a combination of one lumen and a stiff wire provided inside the lumen. However, when the multi-lumen catheter is manipulated, the stiff wire or the inner lumen is not positioned in a center of the multi-lumens. Therefore, one side portion of the multi-lumen catheter which contacts the stiff wire is liable to be damaged or kinked thereat. Further, although the stiff wire provided in the multi-lumens prevents the shaft from being kinked, a certain kind of catheter, such as Over The Wire PTCA catheter, does not have enough space to accommodate the stiff wire therein.

The invention has been made to obviate the foregoing difficulties, and an object of the invention is to provide a shaft for a catheter system, which is flexible and has sufficient stiffness to be manipulated easily without being kinked.

Another object of the invention is to provide a shaft for a catheter system as stated above, wherein an inner lumen or shaft can be easily assembled with an outer lumen.

A further object of the invention is to provide a shaft for a catheter system as stated above, wherein the inner lumen or shaft can be located in a center of the outer lumen.

Further objects and advantages of the invention will be apparent from the following description of the invention.

SUMMARY OF THE INVENTION

In accordance with the present invention, a shaft is used for a catheter system for PTCA, angiography, perfusion, drug delivery or the like. The catheter system is formed of a head, a shaft and a handle connected together.

When the catheter system is used, first, the head is introduced into a vessel, such as a blood vessel, and is pushed by the handle through the shaft to allow the head to move or proceed deeply in the blood vessel and reach a desire position of the body. The head must sometimes pass through a constricted portion of the blood vessel while enlarging the constricted portion. Therefore, the shaft used in the catheter system is required to have a certain stiffness, flexibility and a light weight.

In the invention, the shaft for the catheter system is formed of an elongated tube made of a flexible material, and a plurality of ribs projecting inwardly from the inner wall of the tube. The ribs are arranged parallel to each other to have a space between the two ribs situated adjacent to each other and extend along a longitudinal direction of the tube. Thus, the shaft has flexibility and stiffness to manipulate the catheter system.

When the catheter system is manipulated, since the respective ribs have a certain thickness, the ribs provide resistant force against a direction in which the shaft is bent to thereby prevent the shaft from being kinked, as well as transmit force or torque for manipulating the head of the catheter system from the handle. Since the ribs are formed, the portions between the ribs can be made thin. Thus, the weight of the shaft can be made light.

Further, the lumen-may accommodate therein an inner lumen or a stiff wire. The inner tube or the stiff wire is positioned in a center of the lumen by means of the ribs projecting from the inner wall of the lumen. Thus, the shaft is prevented from being kinked and at the same time force or torque for manipulating the catheter system is efficiently transmitted from a proximal end to a distal end of the shaft.

DETAILED DESCRIPTION OF PREFERRED EMBODIMENTS

Figure 1:
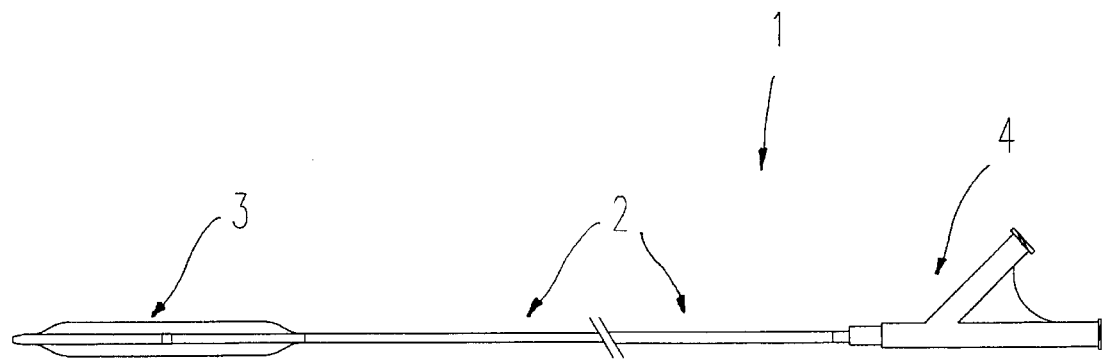
FIG. 1 is a perspective view of a catheter system according to the invention.
Figure 2:
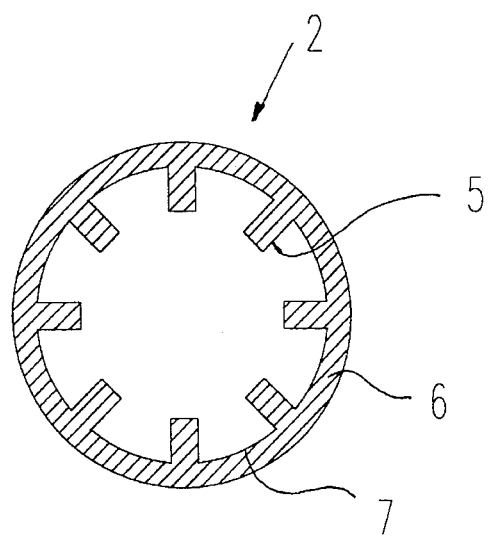
FIG. 2 is a section view of a first embodiment of a shaft of the invention.

Referring to FIGS. 1 and 2, one catheter system 1 is shown. The catheter system 1 includes a shaft 2, a balloon 3 connected to an end of shaft 2, and a handle 4 connected to the other end of the shaft 2. When the catheter system 1 is used, the balloon 3 is introduced into a blood vessel while manipulating the shaft 2 by the handle 4.

The shaft 2 is formed of a tube or lumen 6, and a plurality of ribs 5 projecting inwardly from an inner wall 7 of the lumen 6. The ribs 5 extend parallel to each other along the longitudinal direction of the shaft 2. Each rib 5 has a rectangle shape in a cross section and has a certain thickness. Therefore, the ribs 5 can provide resisting force against a direction that the shaft 2 is bent or kinked, and efficiently transmit force or torque for manipulating the catheter system 1 from a proximal end to a distal end of the shaft 2.

The lumen 6 is made of a stiff, flexible and light material, such as a polymeric resin. The ribs 5 can be made integrally at a time of extruding the lumen 6.

In FIG. 2, the rib 5 has a rectangular shape, but the corners of the rib 5 may be made smooth. The rib 5 may have a corrugated shape. The height and width of the rib 5 are determined based on the requirement of the shaft 2.

Figure 3:
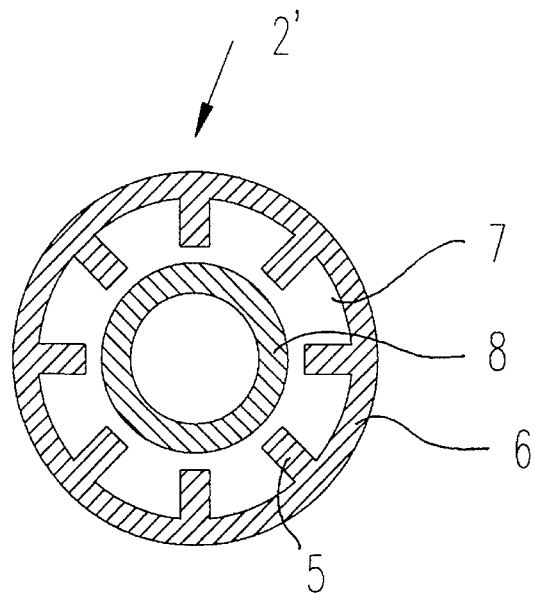
FIG. 3 is a section view of a second embodiment of a shaft of the invention.

FIG. 3 shows a second embodiment of a shaft 2' of the invention. The shaft 2' includes an inner lumen 8 provided in the lumen 6 with a plurality of ribs 5 as disclosed in the first embodiment. The lumen 6 accommodates the inner lumen 8 therein so that the lumens 6, 8 extend parallel to each other. Namely, the inner lumen 8 is held in a center of the lumen 6 by means of the ribs 5. When a catheter system 1 is manipulated, the inner lumen 8 is held in the center of the outer lumen 6. The lumens 6, 8 prevent the shaft from being kinked.

In the second embodiment, a wire or other materials can smoothly pass through the inner lumen 8. Further, two separate paths extending between the distal and proximal ends of the shaft can be established, which is useful in using the catheter system.

Figure 4:
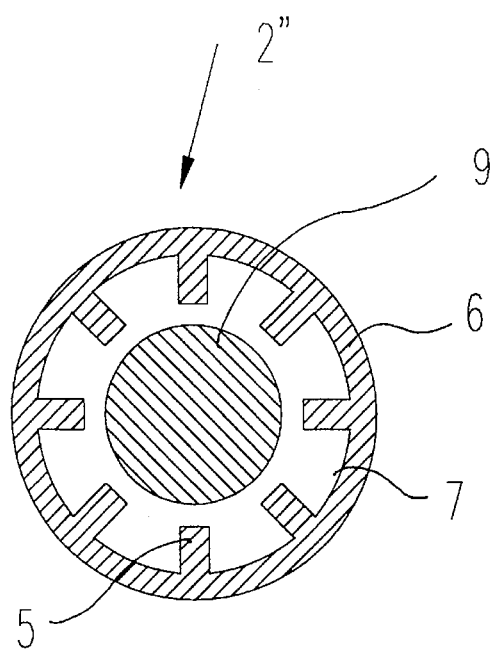
FIG. 4 is a section view of a third embodiment of a shaft of the invention.

FIG. 4 shows a third embodiment of a shaft 2" of the invention. The shaft 2" is formed of a stiff wire 9, and the lumen 6 having a plurality of ribs 5 as explained in the first embodiment. The stiff wire 9 is located and held in a center of the lumen 6 by means of the ribs 5. The wire 9 functions to stiffen the shaft 2" more strongly.

As described above, in the shaft of the invention, since the lumen is provided with a plurality of ribs and the respective ribs have a certain thickness, the shaft is not kinked nor weakened easily and transmits force or torque for manipulating a catheter system from the proximal end to the distal end properly. Since the lumen of the invention is stiff enough without accommodating a stiff wire or an inner lumen therein, the lumen has an enough space therein Further, if the lumen is provided with a stiff wire or an inner lumen therein, the obtained shaft can be further strengthened, While the invention has been explained with reference to the specific embodiments of the invention, the explanation is illustrative and the invention is limited only by the appended claims.

What is claimed is:

1. A shaft for a catheter system introduced into a vascular system, comprising:

an elongated tube made of a flexible material and having an inner wall, said tube having an equal thickness in radial and longitudinal directions; and a plurality of ribs projecting radially inwardly from the inner wall of said tube and being integrally formed with said tube, said ribs having constant and equal heights and widths and being arranged parallel to each other to have an equal space between two ribs situated adjacent to each other, each of Said ribs having a substantially rectangular shape in cross section perpendicular to a longitudinal direction of the tube, said ribs extending from a proximal end to a distal end of the shaft along a longitudinal direction of said tube so that said shaft has flexibility and stiffness to manipulate the catheter system.

2. A shaft according to claim 1, further comprising an inner tube positioned in a center of the elongated tube and held by said ribs, said inner tube preventing the shaft from being kinked in use.

3. A shaft according to claim 1, further comprising a wire positioned in a center of the elongated tube and held by said ribs, said wire preventing the shaft from being kinked in use.

4. A shaft according to claim 3, wherein the plurality of ribs and the wire are spaced away from each other.

* * * * *